(12) United States Patent
Fischer et al.

(10) Patent No.: US 6,303,828 B1
(45) Date of Patent: Oct. 16, 2001

(54) PROCESS FOR SELECTIVE CATALYTIC OXIDATION OF OLEFINS TO ALDEHYDES, KETONES WITH CLEAVAGE OF C=C BONDS

(75) Inventors: Richard Walter Fischer, Oberhausen; Wolfgang Anton Herrmann, Freising; Thomas Weskamp, München, all of (DE)

(73) Assignee: Aventis Research & Technologies GmbH & Co. KG, Frankurt am Main (DE)

( * ) Notice: Subject to any disclaimer, the term of this patent is extended or adjusted under 35 U.S.C. 154(b) by 0 days.

(21) Appl. No.: 09/403,459

(22) PCT Filed: Mar. 31, 1998

(86) PCT No.: PCT/EP98/01862

§ 371 Date: Feb. 11, 2000

§ 102(e) Date: Feb. 11, 2000

(87) PCT Pub. No.: WO98/47847

PCT Pub. Date: Oct. 29, 1998

(30) Foreign Application Priority Data

Apr. 24, 1997 (DE) .............................. 197 17 181

(51) Int. Cl.[7] .............................. C07C 45/00; B01J 31/00
(52) U.S. Cl. .......................... 568/430; 568/485; 502/167
(58) Field of Search .................... 568/430, 485; 502/167

(56) References Cited

U.S. PATENT DOCUMENTS

| | | | |
|---|---|---|---|
| 3,518,285 | 6/1970 | Fenton et al. ...................... 260/348.5 |
| 4,560,803 | * 12/1985 | Yah et al. .............................. 568/401 |
| 4,859,799 | 8/1989 | Campestrini et al. ................ 568/430 |
| 5,126,490 | * 6/1992 | Schwartz et al. ..................... 568/320 |
| 5,155,247 | 10/1992 | Herrmann et al. ..................... 556/46 |
| 5,321,158 | 6/1994 | Warwel et al. ....................... 562/544 |

* cited by examiner

*Primary Examiner*—Porfirio Nazario-Gonzalez
(74) *Attorney, Agent, or Firm*—Frommer Lawrence & Huag LLP

(57) ABSTRACT

The use of compounds of the formula (I)

Figure 1:
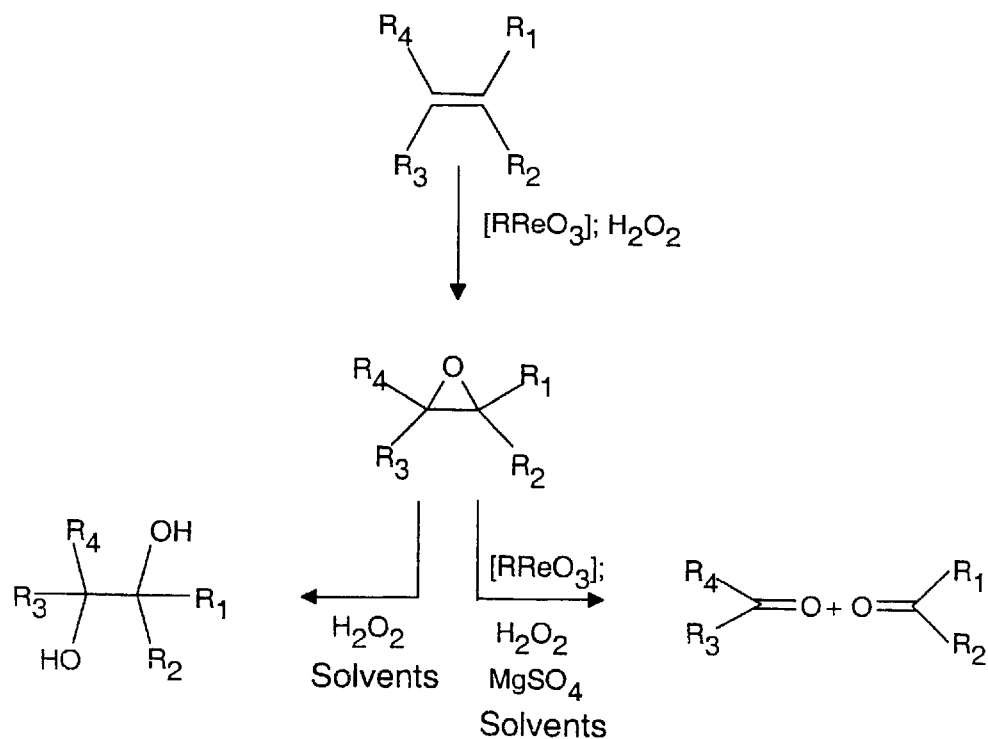

$$R^1_a Re_b O_c \cdot L_d \qquad (I),$$

in which
- a=zero or an integer from 0 to 6
- b=an integer from 1 to 4
- c=an integer from 1 to 12
- d=an integer from 0 to 4
- L=Lewis base and the total of a, b and c is such as to comply with the penta- or hepta-valency of rhenium, with the proviso that c is not greater than 3·b, and in which $R^1$ is absent, identical or different and is an aliphatic hydrocarbon radical having 1 to 10 carbon atoms, an aromatic hydrocarbon radical having 6 to 10 carbon atoms or an arylalkyl radical having 7 to 9 carbon atoms, where the $R^1$ radicals can, where appropriate, be substituted identically or differently, independently of one another, as catalysts for the selective oxidation of olefins with cleavage of C=C bonds to give the corresponding carbonyl compounds in the presence of a peroxide-containing compound, where the amount of substance ratio of olefin to peroxide-containing compound is in a range from 1:2 to 1:14.

6 Claims, 1 Drawing Sheet conventional course of the reaction in the presence of stoichiometric amounts of water novel reaction route using anhydrous conditions or specific solvent systems $R_1, R_2, R_3, R_4$ = H or $(CH_2)_x$-$CH_3$ with x = 0 to 60 conventional course of the reaction in the presence of stoichiometric amounts of water novel reaction route using anhydrous conditions or specific solvent systems $R_1, R_2, R_3, R_4 = H$ or $(CH_2)_x\text{-}CH_3$ with $x = 0$ to $60$

PROCESS FOR SELECTIVE CATALYTIC OXIDATION OF OLEFINS TO ALDEHYDES, KETONES WITH CLEAVAGE OF C=C BONDS

The present invention relates to the use of certain organorhenium compounds for the selective catalytic oxidation of olefins to the corresponding carbonyl compounds with cleavage of C=C bonds, and to a process therefor.

The dominant methods for oxidizing olefins to carboxylic acids and aldehydes with cleavage of C=C bonds are still those characterized by stoichiometric use of the oxidizing agent ($CrO_3/H_2SO_4$, manganese compounds, $RuO_4$). These processes suffer not only from the ecological and economic problem of the production of inorganic salts, which makes elaborate and thus costly purification of the wastewater necessary, but also from a lack of acceptability in health and pharmacology terms, and a lack of selectivity concerning the synthesis of aldehydes. In addition, oxidation with these reagents results exclusively in carboxylic acids because the aldehydes produced as intermediates undergo immediate further reaction and cannot be isolated.

The only systems which can be said to be efficient to date in the area of catalytic processes for cleavage of C=C bonds are those in which ruthenium compounds are employed as catalysts (R. A. Sheldon, J. Kochi, Metal-Catalyzed Oxidation of Organic Compounds, Academic Press, New York, 1981). However, the advantage of a catalytic process in oxidative chemistry becomes really evident only when the primary oxidizing agent employed is ecologically acceptable. Ruthenium compounds have the disadvantage in this respect of being incompatible with the ecologically acceptable hydrogen peroxide as primary oxidizing agent (reaction product water), because with this there is rapid, and sometimes even explosive, decomposition. The oxidizing agents which are therefore employed in conjunction with ruthenium complexes (peracetic acid, NaOCl, $NaIO_4$ etc.) on the one hand prove to be complicated and costly in process engineering terms (peracetic acid), and on the other hand are unable to solve the problem of the production of inorganic salts in the stoichiometric oxidation (NaOCl, $NaIO_4$ etc.). In addition, control of the ruthenium-catalyzed oxidations to give aldehydes is impossible because they are rapidly oxidized further to carboxylic acids.

Thus, in particular, access to aliphatic aldehydes has hitherto been essentially reserved to the hydroformylation reaction, which likewise starts from the olefins obtainable from the SHOP process but, in contrast to the bond-cleaving oxidation, generates the required aldehyde by extending the carbon chain using carbon monoxide.

Transition metals which are compatible with hydrogen peroxide (Mo, W, Re) are at present suitable only for epoxidation in good yields. Cleavages of C=C bonds take place, if at all, only with poor yields (C. Venturello, M. Ricci, J. Org. Chem. 1986, 51, 1599; G. W. Parshall, U.S. 3646130). These systems are, however, unsuitable for selective generation of aldehydes.

In the area of rhenium chemistry, studies by Buchler et al. (DE-A-373 189, DE-A-3 731 690) have shown that rhenium complexes are capable of epoxidizing alkenes.

EP-A-380 085 discloses organorhenium compounds which are employed as catalysts for oxidizing olefins to the corresponding epoxyalkanes and diols in the presence of hydrogen peroxide.

Where EP 0 380 085 relates to oxidation to carbonyl compounds, this takes place either without cleavage of bonds, or has been demonstrated only for the oxidation of stilbene. G. W. Parshall is able with the $Re_2O_7/H_2O_2$ system to oxidize cyclododecane to 1,12-dodecanoic acid (U.S. Pat. No. 3,646,130), although the selectivities are economically unacceptable.

The object therefore is to find an efficient catalyst system which makes the corresponding carbonyl compound, in particular the aldehyde, as the missing link in the chain of oxidation olefin-epoxyalkane or alkanediol-alkanal-alkanoic acid, available in high selectivity with cleavage of C=C double bond in the olefin employed.

It has been found that certain organorhenium compounds are suitable as highly active catalysts for the oxidation of olefins selectively to aldehydes or ketones with cleavage of the C=C double bond when they are used with peroxide-containing compounds in a liquid medium. This is all the more surprising since the rhenium catalysts employed have to date been distinguished, besides their high activity (W. A. Herrmann, R. W. Fischer, D. W. Marz, Angew. Chem. 1991, 103, 1706), very particularly by their high selectivity for the oxidation of olefins to the epoxides and, where appropriate, to the diols formed subsequently by hydrolysis.

The invention thus relates to the use of compounds of the formula $$R^1_a Re_b O_c \cdot L_d \qquad (I),$$

in which a=zero or an integer from 0 to 6
b=an integer from 1 to 4
c=an integer from 1 to 12
d=an integer from 0 to 4
L=Lewis base and the total of a, b and c is such as to comply with the penta-or hepta-valency of rhenium, with the proviso that c is not greater than 3•b, and in which $R^1$ is absent or identical or different, and is an aliphatic hydrocarbon radical having 1 to 20 and preferably having 1 to 10 carbon atoms, an aromatic hydrocarbon radical having 6 to 20 and preferably having 6 to 10 carbon atoms or an arylalkyl radical having 7 to 20 and preferably having 7 to 9 carbon atoms, where the $R^1$ radicals can, where appropriate, be substituted identically or differently, independently of one another, and in the case of δ-bonded radicals at least one hydrogen atom is still bonded to the carbon atom in the α position, as catalysts for the selective oxidation of olefins with cleavage of C=C bonds to give the corresponding carbonyl compounds in the presence of a peroxide-containing compound, where the amount of substance ratio of olefinic double bond to peroxide-containing compound is in a range from 1:2 to 1:14.

The present invention further relates to a process for the selective oxidation of olefins to the corresponding carbonyl compounds with cleavage of C=C bonds, where the olefins are oxidized in the presence of a catalyst of the formula I $$R^1_a Re_b O_c \cdot L_d \qquad (I),$$

in which $R^1$, a, b, c, d and L have the abovementioned meaning, in a liquid medium with a peroxide-containing compound, and the amount of substance ratio of olefinic double bond to peroxide-containing compound is in a range from 1:2 to 1:14.

FIG. 1 shows for the example of compounds of the formula $RReO_3$ how they can be employed as adaptable catalysts for epoxidation, vicinal dihydroxylation and cleavage of C=C bonds with selective generation of aldehydes.

The compounds of the formula (I) may also be in the form of their Lewis base adducts. Typical examples of Lewis bases are pyridine, bipyridine, t-butylpyridine, amines, in particular secondary and tertiary amines such as triethylamine and quinuclidine, $H_2O$ and polyethers such as, for example, diglyme.

An aliphatic hydrocarbon radical $R^1$ means alkyl radicals having 1 to 20 and preferably having 1 to 10 carbon atoms, alkenyl or alkynyl radicals having 2 to 20 and preferably having 2 to 10 carbon atoms, cycloalkyl or cycloalkenyl radicals having 3 to 20 and preferably having 3 to 10 carbon atoms. Suitable examples of $R^1$ are alkyl radicals such as methyl, ethyl, propyl, isopropyl and the various butyl, pentyl, hexyl, octyl radicals such as ethylhexyl and decyl radicals, and alkenyl radicals such as allyl; also suitable are cycloalkyl radicals such as cyclopropyl, cyclobutyl, cyclopentyl, alkylated cyclohexyl such as hydrogenated tolyl, xylyl, ethylphenyl, cumyl or cymyl, 1-menthyl and 1-norbornyl, and alkenyl radicals such as vinyl and allyl and cycloalkenyl radicals such as cyclopentadienyl and pentamethylcyclopentadienyl, with methyl being particularly preferred.

Suitable examples of an aromatic hydrocarbon radical $R^1$ are phenyl or naphthyl. Benzyl may be mentioned as example of an arylalkyl radical.

The radical $R^1$ can also be substituted. Examples of suitable substituents are fluorine, chlorine, bromine, $NH_2$, $NR^2_2$, $PH_2$, $PHR^2$, $PR^2_2$, OH or $OR^2$, where $R^2$ is identical or different and is an alkyl radical having 1 to 20 and preferably having 1 to 10 carbon atoms or an aryl radical having 6 to 20 and preferably having 6 to 10 carbon atoms, which can, for example, have the meaning mentioned above for $R^1$.

Whereas the alkyl, cycloalkyl and arylalkyl radicals are always δ-bonded to the central Re atom, the alkenyl, alkynyl, cycloalkenyl and aryl radicals $R^1$ can be δ- or π-bonded to the Re center.

Very particularly preferred compounds of the formula (I) are $C_1$–$C_3$–alkyltrioxorhenium complexes such as, for example, the rhenium oxides methylrhenium trioxide ($CH_3ReO_3$), cyclopentadienylrhenium trioxide ($CpReO_3$), cyclopropylrhenium trioxide ($C_3H_5ReO_3$), and dirhenium heptoxide ($Re_2O_7$).

It is for steric reasons beneficial for the compound of the formula (I) to have not more than three groups having more than 6 carbon atoms per rhenium atom; the compounds expediently comprise only one such group.

The olefins to be employed for the use according to the invention are not subject to any particular restrictions.

Examples of suitable compounds with C=C double bonds for the process according to the invention are olefins having 2 to 60 carbon atoms. The olefins may be straight-chain or branched, singly or multiply unsaturated and, where appropriate, substituted.

In the case where a carbon atom of a double bond has no H substituent, such as 2-alkyl-1-alkene compounds, oxidation to the aldehyde is impossible, and the C=C bond on this carbon atom is cleaved to form the corresponding ketones. A typical example of 2-alkyl-1-alkene compounds is 2-ethyl-1-butene.

It is also possible to use olefins of the formula $R^5R^2C=CR^3R^4$ in which the olefinic bond can be part of a carbon chain which is closed to a ring and in which $R^2$ to $R^5$ are identical or different, it being possible for the radicals to be aromatic having 6 to 20 carbon atoms, nonaromatic but olefinically unsaturated, conjugated to or cumulative with the olefinic bond to be oxidized and having 1 to 50 carbon atoms, or saturated alkyl and cycloalkyl chains having 1 to 50 carbon atoms or halogen.

Further suitable examples are the olefins described in EP 0 380 085.

Examples of cycloaliphatic olefins are cyclopentene, cyclohexene, 1-methyl-1-cyclohexene, cycloheptene, cyclooctene, cyclooctadiene, cyclooctatetraene, cyclododecene, cyclohexadecadiene or limonene.

Examples of singly or multiply unsaturated alkenes are propene, isobutene, n-hexene, n-octene, decene, dodecene, 1,9-decadiene, 2-methyl-1-butene, 2,3-dimethyl-2-butene, 2-methyl-1-hexene, 2-bromo-2-butene, 3-methyl-1,2-butadiene, octadecene, 2-ethyl-1-butene.

Suitable aromatic olefins are styrene derivatives and stilbene derivatives.

The stoichiometry of the peroxide-containing compound employed is crucial for the present invention.

The amount of substance ratio of olefinic double bond to peroxide-containing compound according to the invention is from 1:2 to 1:14, preferably 1:4 to 1:7. If the amount of substance ratio is less, no selective oxidation to the corresponding carbonyl compounds, in particular to the aldehydes, takes place.

Examples of suitable peroxide-containing compounds are hydrogen peroxide, inorganic peroxides such as alkali metal peroxides, espeically sodium peroxide, and percarboxylic acids and their salts such as m-chloroperbenzoic acid, peracetic acid, hexamethylperoxodisiloxane, magnesium monoperoxophthalate, t-butyl hydroperoxide and bis-t-butylperoxide with hydrogen peroxide being preferred.

The peroxide-containing compound is preferably employed in the form of an anhydrous oxidizing solution which comprises a homogeneous system consisting of solvent and peroxide-containing compound. The concentration of the peroxide-containing compound in the appropriate solvent is in this case from 1 to 90%, preferably 10% to 50%.

Organic solvents are examples of a suitable liquid medium for the oxidation reaction.

Examples of suitable solvents are diethyl ether, di-n-butyl ether, tetrahydrofuran, acetonitrile, monohydric alcohols having 1 to 5 carbon atoms, such as methanol, ethanol, the various propanols and butanols, aromatic hydrocarbons such as toluene or the xylenes, especially tert-butanol and tert-butyl methyl ether.

In a particularly preferred embodiment, the reaction takes place, for protic and most aprotic solvents, under anhydrous conditions by removing in particular the water of reaction resulting on use of the peroxide-containing compound.

The term "anhydrous conditions" particularly preferably means $c(H_2O)<5$ mol % based on the solvent.

Removal of the water resulting from the peroxide-containing compound during the reaction can take place by adding inorganic or organic substances which are able to absorb water. Examples thereof are $MgSO_4$, $Na_2SO_4$, $CaCl_2$, sulfuric acid or orthoesters of carboxylic acids. Depending on the water-absorbing capacity of the particular compound, 0.05 to 10 mole equivalents are added, based on the amount of peroxide-containing compound employed.

The oxidizing solution is employed in such a way that at least 2, preferably 4, equivalents of peroxide-containing compound are present per equivalent of double bond to be oxidized in the reaction mixture, and even a large excess of peroxide-containing compound does not result in further oxidation of the aldehyde to the carboxylic acid.

The catalyst can be employed in an amount of from 0.01 to 5.0 mol %, preferably 0.01 to 2.0 mol %, calculated as Re metal catalyst based on olefin. The amount of catalyst may also be larger or smaller as required.

In another preferred embodiment, the specific solvents employed are aprotic solvents, in particular tert-butyl methyl ether.

The reaction mixture is normally stirred at a temperature of from 10 to more than 120° C., preferably at 60 to 80° C., until the conversion is complete.

The reaction mixture is then worked up in a manner usual for the skilled worker, i.e. for example filtered and fractionally distilled under reduced pressure.

The organorhenium compounds of the formula (I) and their ability to epoxidize olefins highly selectively are known (EP-A-380 085, DE 3 902 357 Al). Their ability to cleave C=C double bonds and, in the case of unbranched alkenes, to prepare aldehydes selectively is, however, novel and was by no means to be expected. Thus, to date, only ruthenium in its complexes has been known as efficient catalyst for cleaving C=C bonds. The use of alkylrhenium compounds in these reactions has only been made possible by the specific adjustment of the ratio of the amount of olefin (i.e. double bond) to peroxide-containing compound. The reaction according to the invention is assisted in particular by adding an organic or inorganic auxiliary reagent which ensures the absence of water from the system and thus a distinctly increased useful life of the catalyst, which greatly promotes oxidation beyond the epoxide oxidation stage at elevated temperature.

It has also proven advantageous for the useful life of the catalyst to use or add specific aprotic solvents.

The catalysts employed are, by reason of their dissolving properties, extremely suitable as homogeneous catalysts. Their particular advantage is also that they can be synthesized in a simple manner from commercially available $Re_2O_7$ with the aid of conventional substances which act as donors of organic groups, for example in the case of $R^1$ =$CH_3$ by reacting with commercially available tetramethyltin or commercially available dimethylzinc. They are insensitive to air and moisture, can be stored at room temperature, and are, in combination with peroxide-containing compounds, highly active catalysts for the oxidations according to the invention.

Thus the combination of particular organorhenium compounds with a suitable oxidizing agent results in an adjustable catalyst system which, on a comparable basis, results selectively as required in the corresponding epoxides, vicinal diols (DE 3902357 Al) or aldehydes/ketones (compare FIG. 1). The latter is central to this invention, it being possible to fix the particular final product by the choice of the reaction conditions.

EXAMPLES

General Method for the Rhenium-Catalyzed Oxidation of Alkenes with cleavage of C=C bonds to aldehydes/ketones 1. Preparation of the Oxidizing Solution The appropriate amount of hydrogen peroxide (85% in water) is added to the solvent to reach the required concentration of hydrogen peroxide. To avoid unwanted side reactions, the mixture is cooled to 0 to 5° C. To remove the water, the solution is mixed with an amount of magnesium sulfate equivalent to the amount of hydrogen peroxide and is stirred for several hours. The resulting magnesium sulfate hydrate is then filtered off. The peroxide content is determined by iodometry.

2. Alkene Oxidation

The alkenes to be oxidized are mixed with oxidizing solution so that an appropriate amount of hydrogen peroxide is present per alkene. An appropriate amount of desiccant is then added, so that the water produced during the reaction is trapped as quantitatively as possible. Finally, the catalyst is added at the temperatures indicated in the table. The reaction mixture is stirred until conversion of the alkene is complete.

3. Workup

The desiccant is removed as far as possible by filtration and then washed several times with organic solvents. Fractional distillation is then carried out under reduced pressure.

The table which follows indicates the experiments carried out in accordance with the above general method.

As byproducts to the aldehydes which are generated there is formation of the corresponding epoxyalkenes and secondary products thereof with the residual water available. No further reaction beyond the aldehyde oxidation stage to the carboxylic acid is to be observed.

The data on the yield of aldehyde are to be understood as isolated yields except for the data on the oxidation of octadecene, which were found by integrating the $^1$H-NMR signals.

Example 13 shows the oxidation of a branched alkene, and Examples 14 to 17 are comparative examples.

| No. | Alkene | Catalyst | T [° C.] | t [h] | Desiccant | Oxidizing solution | Conversion | Yield |
|---|---|---|---|---|---|---|---|---|
| 1 | 1-Hexene (10 mmol) | MTO (0.10 mmol) | 65 | 7 | $MgSO_4$ | 60 mmol $H_2O_2$/ MTBE | 100% | 68% 1-Pentanal 32% 1,2-Hexanediol |
| 2 | 1-Octene (10 mmol) | MTO (0.10 mmol) | 65 | 7 | $MgSO_4$ | 60 mmol $H_2O_2$/ MTBE | 100% | 65% 1-Heptanal 35% 1,2-Octanediol |
| 3 | 1-Octene (10 mmol) | MTO (0.10 mmol) | 65 | 24 | $Na_2SO_4$ | 60 mmol $H_2O_2$/ MTBE | 100% | 47% 1-Heptanal 53% 1,2-Octanediol |
| 4 | 1-Octene (10 mmol) | MTO (0.10 mmol) | 65 | 7 | $MgSO_4$ | 60 mmol $H_2O_2$/ tert-Butanol | 100% | 50% 1-Heptanal 50% 1,2-Octanediol |
| 5 | 1-Octene (10 mmol) | MTO (0.10 mmol) | 80 | 7 | $MgSO_4$ | 60 mmol $H_2O_2$/ tert-Butanol | 100% | 47% 1-Heptanal 50% 1,2-Octanediol |
| 6 | 1-Octene (10 mmol) | MTO (0.10 mmol) | 65 | 16 | $MgSO_4$ | 120 mmol $H_2O_2$/ tert-Butanol | 100% | 53% 1-Heptanal 47% 1,2-Octanediol |
| 7 | 1-Octene (10 mmol) | MTO (0.10 mmol) | 65 | 7 | $MgSO_4$ | 60 mmol $H_2O_2$/ Acetonitrile | 100% | 32% 1-Heptanal 68% 1,2-Octanediol |
| 8 | 1-Octene (10 mmol) | MTO (0.10 mmol) | 65 | 10 | $MgSO_4$ | 60 mmol $H_2O_2$/ Di-n-butyl ether | 100% | 10% 1-Heptanal 90% 1,2-Octanediol |
| 9 | 1-Octene (10 mmol) | MTO (0.10 mmol) | 65 | 12 | Ethyl orthoformate | 60 mmol $H_2O_2$/ tert-Butanol | 100% | 28% 1-Heptanal 72% 1,2-Octanediol |
| 10 | 1-Decene (10 mmol) | MTO (0.10 mmol) | 65 | 7 | $MgSO_4$ | 60 mmol $H_2O_2$/ MTBE | 100% | 57% 1-Nonanal 53% 1,2-Decanediol |
| 11 | 1-Octadecene | MTO | 65 | 7 | $MgSO_4$ | 60 mmol $H_2O_2$/ | 100% | 52% 1-Octadecanal |

-continued

| No. | Alkene | Catalyst | T [° C.] | t [h] | Desiccant | Oxidizing solution | Conversion | Yield |
|---|---|---|---|---|---|---|---|---|
|  | (10.0 mmol) | (0.10 mmol) |  |  |  | MTBE |  | 48% 1,2-Octadecanediol |
| 12 | 1-Octene (10 mmol) | MTO (0.10 mmol) | 65 | 7 | — | 60 mmol $H_2O_2$/ MTBE | 100% | 58% 1-Heptanal 42% 1,2-Octanediol |
| 13 | 2-Ethyl-1-butene (10 mmol) | MTO (0.10 mmol) | 65 | 7 | $MgSO_4$ | 60 mmol $H_2O_2$/ tert-Butanol | 100% | 76% 3-Pentanone 24% 2-Ethyl-1,2-butanediol |
| 14 | 1-Octene (10 mmol) | — | 65 | 48 | $MgSO_4$ | 60 mmol $H_2O_2$/ tert-Butanol | <5% | >95% 1-Octene (starting material) |
| 15 | 1-Octene (10 mmol) | MTO (0.10 mmol) | 65 | 7 | — | 60 mmol $H_2O_2$/ tert-Butanol | 80% | 43% 1,2-Epoxyoctane 47% 1,2-Octanediol |
| 16 | 1-Octene (10 mmol) | MTO (0.10 mmol) | 65 | 7 | — | 60 mmol $H_2O_2$/ Acetonitrile | 51% | 16% 1,2-Epoxyoctane 35% 1,2-Octanediol |
| 17 | 1-Octene (10 mmol) | MTO (0.10 mmol) | 65 | 7 | — | 60 mmol $H_2O_2$/ Di-n-butyl ether | 43% | 14% 1,2-Epoxyoctane 29% 1,2-Octanediol |

MTO = Methyltrioxorhenium
MTBE = Methyl tert-butyl ether
Hydrogen peroxide concentration in the oxidizing solutions: 30%

What is claimed is:

1. A process for the selective catalytic oxidation of olefins to the corresponding carbonyl compound which comprises oxidizing olefins and a peroxide-containing compound in a liquid medium in the presence of a catalyst, wherein the catalyst is of the formulae $$R^1_a Re_b O_c \cdot L_d \quad (I),$$

in which
a=zero or an integer from 0 to 6
b=an integer from 1 to 4
c=an integer from 1 to 12
d=an integer from 0 to 4
L=Lewis base
and the total of a, b and c is such as to comply with the penta- or heptavalency of rhenium, with the proviso that c is not greater than 3·b, and
in which
R$^1$ is absent or identical or different and is an aliphatic hydrocarbon radical having 1 to 10 carbon atoms, an aromatic hydrocarbon radical having 6 to 10 carbon atoms or an arylalkyl radical having 7 to 9 carbon atoms, where the R$^1$ radicals where appropriate is optionally substituted identically or differently, independently of one another, the ratio of olefinic double bonds to peroxide-containing compound is in a range form 1:2 to 1:14.

2. The process according to claim 1, where the catalyst is a compound of formula (I) wherein
R' is $C_1$–$C_3$ alkyl,
a is 1,
b is 1, and
c is 3.

3. The process according to claim 1, wherein the peroxide-containing compound is hydrogen peroxide in an anhydrous oxidizing solution.

4. The process according to claim 1, wherein the process is anhydrous and is made anhydrous by adding an inorganic or organic dehydrating agent or by adding an aprotic solvent to said process.

5. The process according to claim 4, wherein the apotic solvent is tert-butyl methyl ether.

6. The process according to claim 4, wherein the olefins are oxidized with cleavage of a C=C double bond to aldehydes.

* * * * *